(12) United States Patent
Soccol et al.

(10) Patent No.: US 9,651,514 B2
(45) Date of Patent: May 16, 2017

(54) INTEGRATED PH AND CONDUCTIVITY SENSOR AND MANUFACTURING METHOD THEREOF

(71) Applicant: NXP B.V., Eindhoven (NL)

(72) Inventors: Dimitri Soccol, Heverlee (BE); Matthias Merz, Leuven (BE)

(73) Assignee: NXP B.V., Eindhoven (NL)

( * ) Notice: Subject to any disclaimer, the term of this patent is extended or adjusted under 35 U.S.C. 154(b) by 250 days.

(21) Appl. No.: 14/447,074

(22) Filed: Jul. 30, 2014

(65) Prior Publication Data
US 2014/0374251 A1 Dec. 25, 2014

Related U.S. Application Data

(63) Continuation-in-part of application No. 14/293,677, filed on Jun. 2, 2014, now abandoned, which is a continuation of application No. 13/600,385, filed on Aug. 31, 2012, now Pat. No. 8,742,470.

(30) Foreign Application Priority Data

Sep. 16, 2011 (EP) .................................. 11187700

(51) Int. Cl.
  *G01N 27/403* (2006.01)
  *G01N 27/30* (2006.01)
  *G01N 27/414* (2006.01)

(52) U.S. Cl.
  CPC ....... *G01N 27/302* (2013.01); *G01N 27/4148* (2013.01); *H01L 2224/48091* (2013.01); *H01L 2924/1815* (2013.01); *Y10T 29/49002* (2015.01)

(58) Field of Classification Search
  CPC .......................... G01N 27/302; G01N 27/4148
  USPC ........................................................ 257/253
  See application file for complete search history.

(56) References Cited

U.S. PATENT DOCUMENTS

| 4,020,830 | A | 5/1977 | Johnson et al. |
| 4,940,945 | A | 7/1990 | Littlejohn et al. |
| 5,342,498 | A | 8/1994 | Graves et al. |
| 5,516,697 | A | 5/1996 | Kruzel |
| 5,911,862 | A | 6/1999 | Chan |
| 8,742,470 | B2 | 6/2014 | Merz |

(Continued)

FOREIGN PATENT DOCUMENTS

| CN | 2410639 Y | 12/2000 |
| CN | 101163440 A | 4/2008 |
| EP | 2 287 597 A1 | 2/2011 |

OTHER PUBLICATIONS

Extended European Seach Report for, European Patent Appl. No. 11181700.3, Mar. 3, 2012.

(Continued)

*Primary Examiner* — Anthony Ho (57) ABSTRACT

Disclosed is a pH and conductivity sensor including a carrier comprising a plurality of conductive tracks and an exposed conductive area defining a reference electrode connected to a first track of said plurality of conductive tracks, a sensing device mounted on the carrier and connected to at least a second track of said plurality of conductive tracks, the sensing device including an exposed surface that is sensitive to H$^+$ concentrations, and a plurality of electrodes adjacent to the exposed surface, an encapsulation covering the carrier, said encapsulation including a first cavity exposing a surface of the sensing device, and a second cavity exposing the exposed conductive area.

20 Claims, 7 Drawing Sheets

(56) References Cited

U.S. PATENT DOCUMENTS

2007/0003209 A1     1/2007   Papautsky et al.
2008/0275327 A1   11/2008   Faarbaek et al.
2011/0036913 A1     2/2011   Merz et al.

OTHER PUBLICATIONS

Office Action from Counterpart Application CN 2014033100972970, Apr. 3, 2014.
Simonis, et al., "Miniaturised Reference Electrodes for Field-Effect Sensors Compatible to Siliconi Cihp Technology", Electrochimica Acta 51, 930-937.
Bergveld, P.; "Thirty years of Isfetology, What happened in the past 30 years and what may happen in the next 30 years"; Sensors and Actuators B; Chemical 88; pp. 1-20; (2003).

INTEGRATED PH AND CONDUCTIVITY SENSOR AND MANUFACTURING METHOD THEREOF

This application is a continuation-in-part of application Ser. No. 14/293,677, filed on Jun. 2, 2014 which is a continuation of application Ser. No. 13/600,385, filed on Aug. 31, 2012, now U.S. Pat. No. 8,742,470, which claims priority to a European Application with Application Number 11181700.3 filed on Sep. 16, 2011, which are hereby incorporated by references for all purposes as if fully set forth herein.

TECHNICAL FIELD

Various exemplary embodiments disclosed herein relate generally to a pH sensor including sensing devices and a reference electrode. Embodiments described herein further relate to a method of manufacturing such a pH sensor.

BACKGROUND

In many application domains, measurement of the pH of a solution or substance is important. In the medical field, the measurement of the pH of a patient's blood can give valuable insights into the condition of the patient because pH values that deviate from expected values can indicate that the patient is suffering from some medical condition. pH sensors used in the medical field are typically costly because they must comply with health and safety regulations when blood samples are returned to the patient, and must be highly accurate.

In the food industry, the measurement of the pH of a food product, e.g. dairy products and meat, is often used because the pH is indicative of the condition of the food product. In such application domains, a high volume of measurements may have to be taken, either because of the large volumes of food or because the duration of the time period over which the food is stored. In such application domains, large numbers of (disposable) sensors may be required, which therefore requires the sensors to be cheap.

As is known, one of the main problems with the stability of pH sensors is that the reference electrode potential may not be stable over time, for instance because ion concentrations in a buffer solution to maintain the reference electrode potential leak away. Such buffer solutions may for instance be employed to protect the reference electrode from variations in the same ion concentration in the medium to be analyzed.

For instance, a commonly used reference electrode is a silver chloride electrode in which the reference potential E is defined by the Nernst equation:

$$E = E^0 - \frac{RT}{F} \ln a_{Cl^-}$$

In this equation, $E^0$ is the standard electrode potential, R is the ideal gas constant, T is the temperature, F is Faraday's constant and $a_{Cl^-}$ is the activity or effective concentration of the chloride ions. It will be immediately recognized that a change in the effective chloride concentration has a direct impact on the reference electrode potential E. Many silver chloride reference electrodes include a solution containing $Cl^-$ ions that needs periodic replenishing in order to maintain a stable reference potential.

This approach may not be suitable in application domains where the sensors are operated by staff that are not trained to replenish the reference electrode or perform recalibrations. Moreover, recalibration and refilling may be too expensive or cannot be performed at all for specific process applications, e.g. monitoring of food quality during transport.

Miniaturized pH sensors including reference electrodes have been made in which a plurality of sensors including a pH sensor and a reference sensor have been integrated on a single chip. However, the manufacturing processes of such ICs is rather complex, such that the cost of such devices is prohibitive for low-end application domains such as the food industry and water and soil quality probes.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of exemplary embodiments adequate to allow those of ordinary skill in the art to make and use the inventive concepts will follow in later sections.

The embodiments described herein seek to provide a low-cost pH sensor having an integrated reference electrode with improved lifetime.

The embodiments described herein further seek to provide a method of manufacturing such a pH sensor.

The embodiments described herein further seek to provide for the multiple integration of pH, temperature and electrical conductivity determination into a single CMOS-compatible solution and allows for a major scale-down and cost reduction of the current state of the art.

According to one embodiment, there is provided a pH and conductivity sensor including a carrier that includes a plurality of conductive tracks and an exposed conductive area defining a reference electrode connected to a first track of said plurality of conductive tracks, a sensing device mounted on the carrier and connected to at least a second track of said plurality of conductive tracks, the sensing device including an exposed surface that is sensitive to $H^+$ concentrations, and a plurality of electrodes adjacent to the exposed surface, an encapsulation covering the carrier, said encapsulation including a first cavity exposing a surface of the sensing device, and a second cavity exposing the exposed conductive area.

The second cavity may include a reference electrode material and an ion reservoir material that share at least one ion type with said reference electrode material, the reference electrode material being positioned between the exposed conductive area and the ion reservoir material.

This pH and conductivity sensor may be manufactured in a cost-effective manner as the footprint of the sensing device does not need to be increased because the reference electrode is incorporated in the package rather than the sensing device whilst the reference electrode at the same time provides a stable reference electrode potential due to the fact that the ion reservoir material, e.g. a gel containing a chloride salt solution such as a silver, potassium or sodium chloride solution, provides a chloride reservoir for the reference electrode material that defines the reference potential of the reference electrode, e.g. an Ag/AgCl paste, thereby ensuring that the chloride activity $a_{Cl^-}$ remains constant for the reference electrode formed by the reference electrode material and the exposed conductive area such as a bond pad, contact pad, landing or mounting pad and so on. Other suitable reference electrolytes may of course also be used.

The pH and conductivity sensor may further include a partially or completely impermeable layer to the ion type in the ion reservoir material over the second cavity. This ensures that the chloride ion concentration in the reference electrode remains constant for prolonged periods of time, thus extending the lifetime of the pH sensor.

In an alternative embodiment, the encapsulation further includes a fluid channel laterally extending from an edge of the encapsulation to the second cavity to keep the reference electrode in contact with the sample. The dimensions of the fluid channel, e.g. its diameter, are chosen such that the ions from the ion reservoir material, i.e. the reference electrolyte cannot (easily) escape the second cavity through the fluid channel, thus avoiding the large out-diffusion of chloride ions from the ion reservoir material. This may for instance be achieved by ensuring that the ion reservoir material has a large enough viscosity to prevent it from entering the fluid channel, and/or by dimensioning the fluid channel such that the contact area between the ion reservoir material and an external medium is reduced to such an extent that the out-diffusion of the relevant ions, e.g. chloride ions, is limited to insignificant amounts.

In yet another embodiment, the encapsulation further includes a further fluid channel laterally extending from the edge to the first cavity. This establishes a liquid connection between the sensing device and the reference electrode, which prevents the pH sensor from floating due to the fact that a permanent liquid/fluid connection between the reference electrode and surface of sensing device or electrode is maintained, thus for instance preventing the occurrence of voltage spikes upon insertion of the pH sensor in a substance containing the analyte of interest.

In an embodiment, the pH sensor further includes a first contact pad connected to the sensing device via one of the other of the conductive tracks and a second contact pad connected to the exposed conductive area via the one of the conductive tracks. This allows for an off-sensor processing of the sensing signals.

The plurality of electrodes may be arranged in parallel or may be interdigitated. A protective layer of $Ta_2O_5$ may be formed on the plurality of electrodes.

Alternatively, the sensing device includes a transceiver, the pH sensor further including an antenna on the carrier connected to the at least one other of the conductive tracks. This allows for on-chip processing of the sensing signals, for instance if the exposed conductive area pad is connected to the sensing device via the second conductive track. The sensing device, e.g. an integrated circuit (IC) includes a pH-sensitive surface such as an ion sensitive field effect transistor having its gate exposed in the first cavity, may be adapted to send the result of the sensing signal processing to a remote receiver, e.g. via a radio-frequency communication protocol.

In an embodiment, the carrier is a printed circuit board. This has the advantage that the first and second conductive tracks may be integral to the printed circuit board.

The pH and conductivity sensor may further include a sharp tip to facilitate inserting the pH sensor into a substance such as a meat product. If such a sharp tip is combined with the presence of the first fluid channel, it is preferred that the first fluid channel is displaced with respect to the lateral axis through the sharp tip, such that the risk of blockage of the fluid channel by the substance upon its penetration is reduced.

In accordance with another embodiment, there is provided a method of manufacturing such a pH and conductivity sensor, including providing a carrier having on its surface a plurality of conductive tracks, an exposed conductive area connected to one of the conductive tracks and a further exposed conductive area fixating an integrated circuit die to the further exposed conductive area, the integrated circuit die including an exposed pH-sensitive surface and a plurality of electrodes adjacent to the pH-sensitive surface, encapsulating the resultant structure in a protective resin, forming first and second cavities in the protective resin, the first cavity exposing the pH-sensitive surface and the second cavity exposing the exposed conductive area, depositing a reference electrode material over the exposed conductive area, and depositing an ion reservoir material sharing at least one ion type with the reference electrode material over the reference electrode material.

In accordance with another embodiment, there is provided a non-transitory machine-readable storage medium encoded with instructions for measuring a pH and conductivity of an analyte on a substrate, the method comprising: method of measuring the pH and conductivity of an analyte on a substrate, the method including exposing a conductive area defining a reference electrode to an analyte of interest, exposing a sensing device comprising a pH-sensitive surface, a plurality of electrodes, and a protection layer to the analyte of interest, determining the pH of the analyte of interest based on measurements taken by the reference electrode and the sensing device, and determining the conductivity of the analyte by determining an overall impedance between the electrodes.

The protection layer may be formed on the pH-sensitive surface and the plurality of electrodes. A resistance of the analyte may be determined by compensating for a capacitance of the substrate and a capacitance of the protection layer.

The method of claim may further include determining a temperature of the analyte based on measurements taken by the reference electrode and the sensing device.

This method has the advantage that a reference electrode can be provided in the packaging process of the pH sensor in a straightforward and therefore cost-effective manner.

Preferably, the encapsulating step and the cavities forming step are performed simultaneously. This provides an extremely cost-effective method of manufacturing the pH sensor of the embodiments described herein as the encapsulation process, e.g. an overmolding process such as the Boschman process in which the cavities are defined as exclusion areas, does not require additional processing steps to form the cavities in the encapsulation.

BRIEF DESCRIPTION OF THE DRAWINGS

Exemplary embodiments of the invention are described in more detail and by way of non-limiting examples with reference to the accompanying drawings, wherein.

DETAILED DESCRIPTION

It should be understood that the Figures are merely schematic and are not drawn to scale. It should also be understood that the same reference numerals are used throughout the Figures to indicate the same or similar parts.

The descriptions and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. As used herein, the terms "context" and "context object" will be understood to be synonymous, unless otherwise indicated.

In agriculture or agribusiness, water and soil quality probes make use of pH, temperature and electrical conductivity sensors, linked to salinity or total dissolved solids (TDS). Although these parameters are used in drinking water quality standards, an important application field is general water quality assessment of surface water, not focusing on specific pollutants.

There exist in the art several portable or handheld multi-integrated products to measure water and soil quality by various companies such as Metrohm, Stevens Water (Hydrolab Series 5) and YSI (Exo and V2 series). However, these devices are bulky and expensive, compared to what can be accomplished using CMOS technology that relies on a combination of several discrete probes to perform the various measurements.

In these commercial solutions, the conductivity probe includes several noble metal electrodes to avoid corrosion/attack by aggressive solutions. Such electrodes are not CMOS compatible. Current hand-held or portable multi-sensors rely on the combination of several probes into a single electronic read-out unit. These are produced separately and form bulky combined probes. There is a need in the art for a probe in which multiple electrodes can be spaced apart on a single probe to improve the linearity and conductivity range of the probe.

Figure 1A:
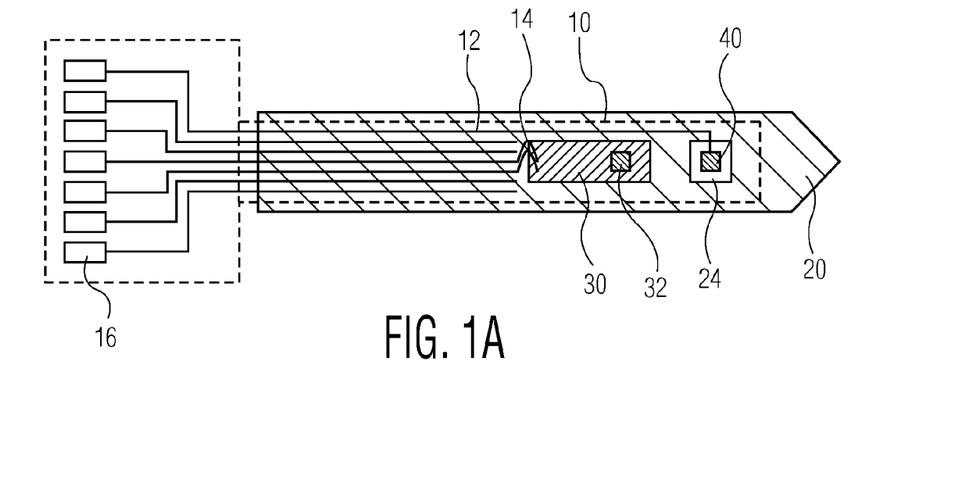
FIG. 1A schematically illustrates a top view of an intermediate device according to an embodiment.
Figure 2:
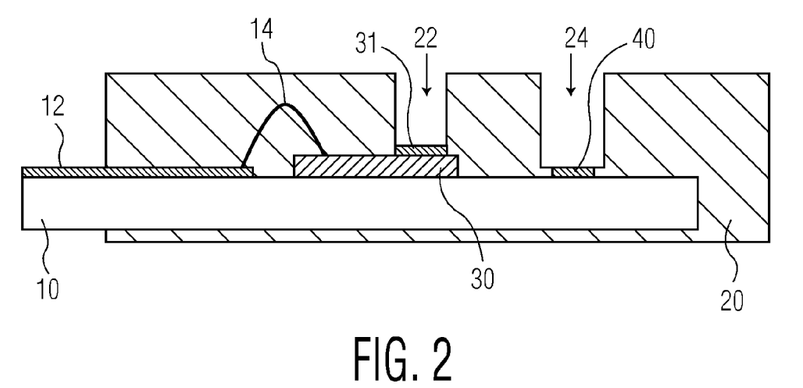
FIG. 2 schematically illustrates a cross section of the intermediate device of FIG. 1.

FIG. 1A schematically illustrates a top view, and FIG. 2 schematically illustrates a cross-section of an intermediate structure of a pH sensor according to a first embodiment. A carrier 10 such as a laminate or a printed circuit board (PCB) is equipped with a plurality of conductive tracks 12 such as a ribbon connector or metal tracks on the carrier, which connect to a plurality of contact pads 16. A sensing device 30 is attached to the carrier 10 in any suitable manner, for instance by adhesion to an exposed metal area such as a landing or mounting pad. The sensing device 30 has an exposed surface 32 of an electrode 31 (illustrated in FIG. 2), also referred to as a gate electrode or sensing electrode, that is pH-sensitive, that is, the exposed surface 32 can be used to detect the pH of a substance brought into contact with the exposed surface 32.

Figure 1B:
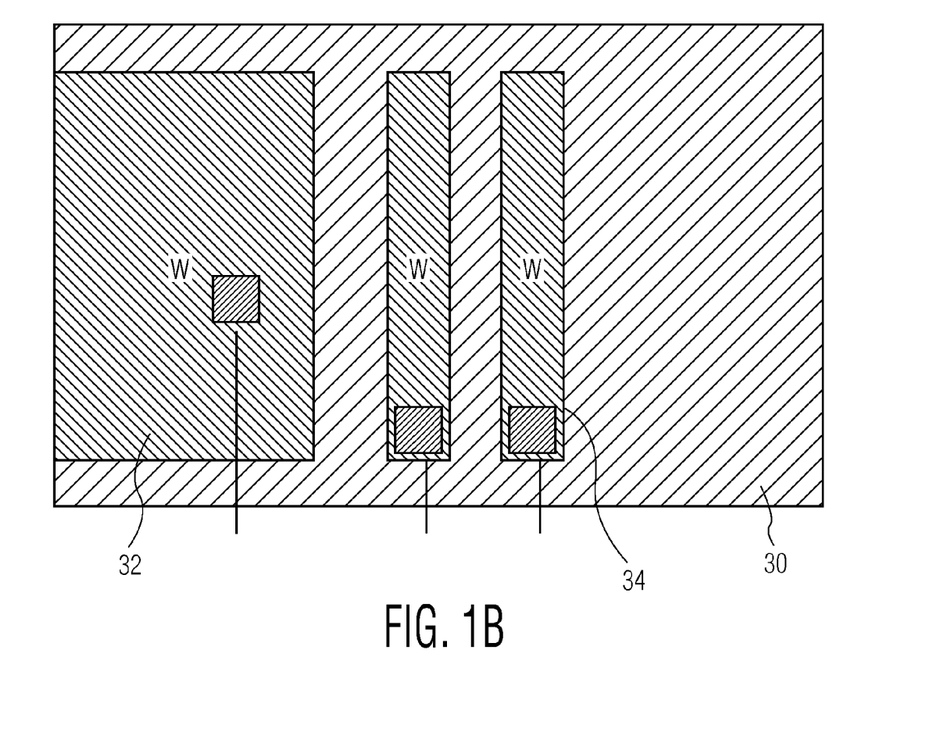
FIG. 1B schematically illustrates an exploded top view of the sensing device of FIG. 1.

FIG. 1B schematically illustrates an exploded top view of the sensing device of FIG. 1. The sensing device 30 has formed thereon the exposed surface 32 of the electrode 31 that acts as the gate of an ISFET to measure pH of an analyte of interest. The sensing device 30 also includes a plurality of electrodes 34 that may be arranged in a parallel configuration. The electrodes 34 also include an exposed surface and are used to measure the electrical conductivity of the analyte of interest.

Figure 1C:
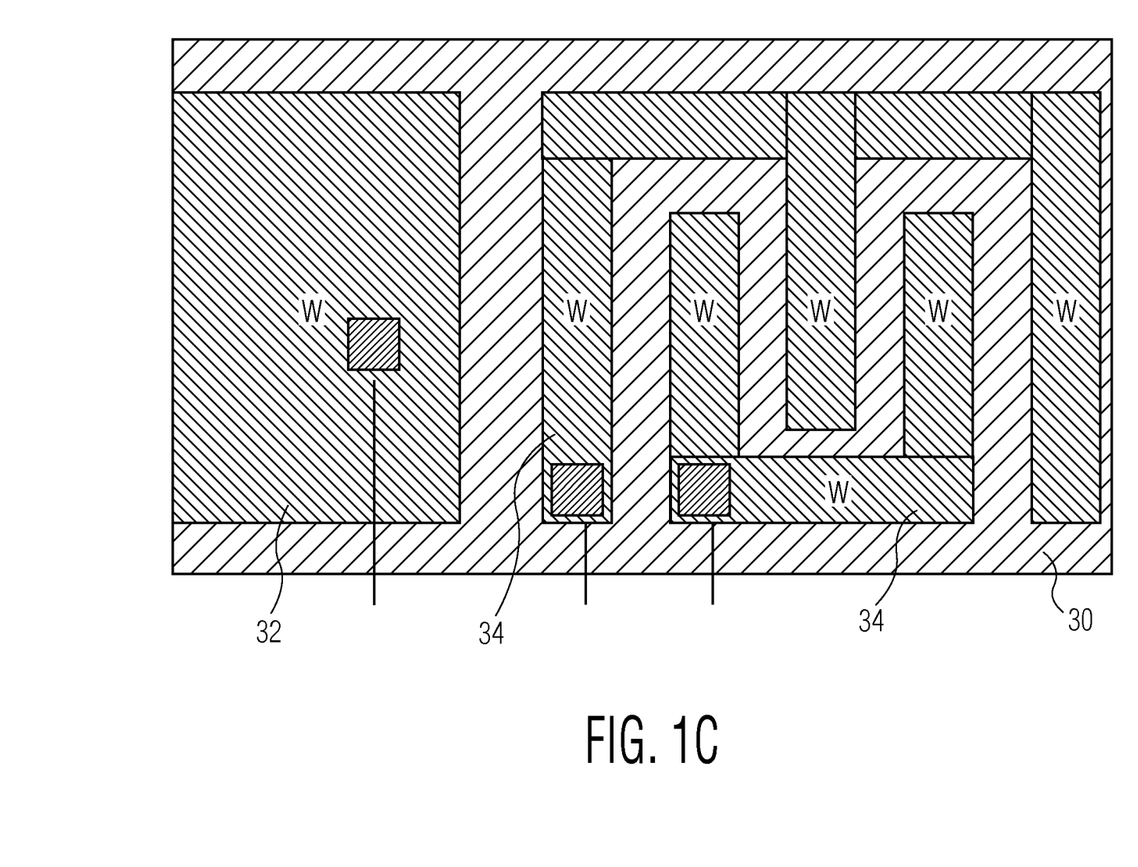
FIG. 1C schematically illustrates an exploded top view of another embodiment.

FIG. 1C schematically illustrates an exploded top view of another embodiment. As illustrated in FIG. 1C, electrodes 34 are patterned in an interdigital arrangement. By providing the electrodes 34 over a large surface area, an increased capacitance for better signal to noise ratio can be obtained.

In an embodiment, the sensing device 30 is a chip or integrated circuit (IC) die that includes an ion-sensitive field effect transistor (ISFET), which has a gate to which the exposed surface 32 belongs. The gate may for instance be an extended gate, which may for instance be connected to an electrode on top of the metallization stack of the IC, and which may be made pH-sensitive by at least providing a coating of a pH-sensitive material such as $Ta_2O_5$ on the exposed surface 32 of the gate electrode 31. After the exposed electrodes 34 are formed, the $Ta_2O_5$ layer 36 is also formed atop the electrodes 34. Extended gate ISFETs are known in the art. As any suitable type of sensing device 30 may be used in the pH sensor of the embodiments described herein, the design of such sensing devices, and in particular of pH-sensitive ISFETs will not be described in further detail for the sake of brevity only.

The sensing device 30, e.g. IC die includes at least one ISFET and electrodes 34, may be connected to the conductive tracks 12 using any suitable connection means 14, e.g. bond wires or stud bumps. This facilitates access to the IC sensing die via the contact pads 16. The contact pads 16 are used to connect the sensing device 30 for power supply and as a data interface. The carrier 10 further includes an exposed conductive area 40, e.g. a contact pad, bond pad, landing pad, mounting pad, an extended portion of a conductive track and so on, which may be made of any suitable material. As a non-limiting example, the exposed conductive area 40 may be a gold-plated copper contact pad. In the embodiment of the pH sensor illustrated in FIG. 1 and FIG. 2, the conductive area 40 is connected to one of the contact pads 16 via one of the conductive tracks 12.

The pH sensor is at least partially covered by an encapsulation 20, which protects the various components of the pH sensor from exposure to external elements, e.g. air, moisture, liquids and/or the analyte of interest. The encapsulation 20 may be formed in any suitable manner, e.g. over molding or injection molding, as will be explained in more detail later. The encapsulation 20 typically covers at least part of the carrier 10, the conductive tracks 12 and the sensing device 30. Any suitable molding material may be used, e.g. epoxy- or silicone-based compounds. The encapsulation 20 includes a first cavity 22, which exposes the exposed surface 32 that is pH-sensitive, electrodes 34 and a second cavity 24, which exposes the conductive area 40. The first cavity 22 and the second cavity 24 may have any suitable dimensions. The pH sensor may further include a sharp tip 21 to facilitate easy insertion of the pH sensor into a substance of interest, e.g. a meat sample or soil sample.

Figure 3:
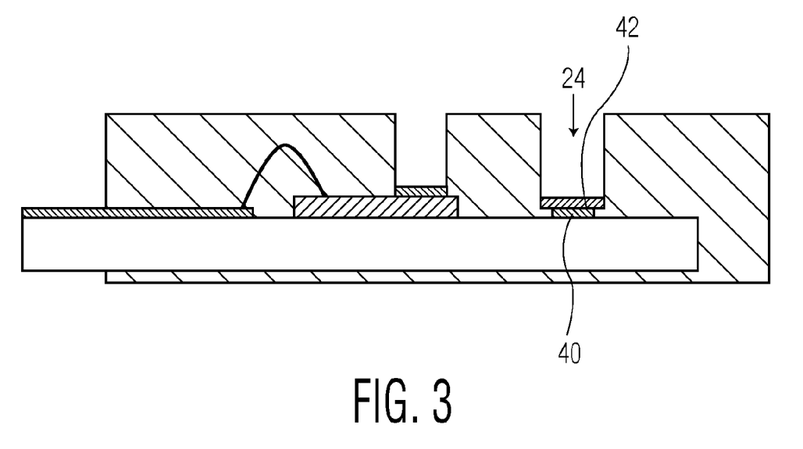
FIG. 3-5 schematically illustrate various steps of a method of completing the intermediate device of FIGS. 1 and 2.
Figure 4:
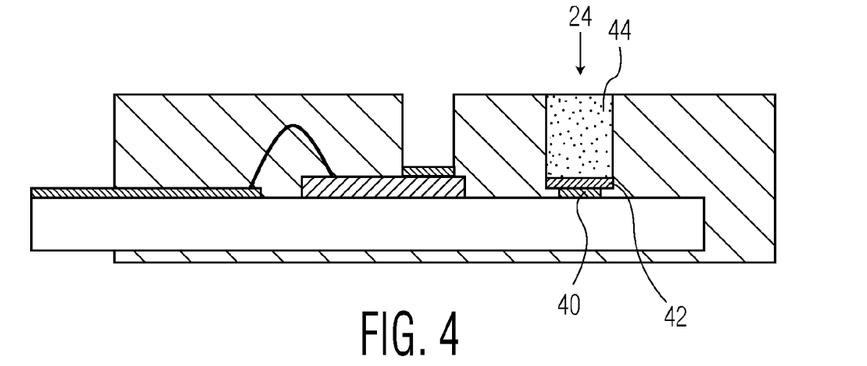
Figure 5:
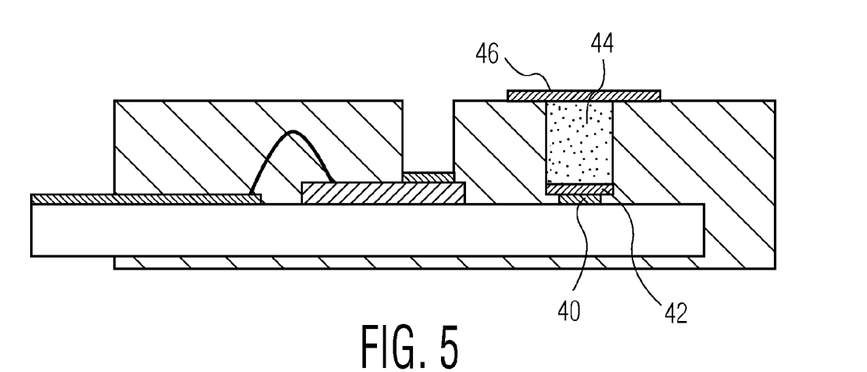

The conductive area 40 exposed by the second cavity 24 forms part of the reference electrode of the pH sensor, which may be formed as illustrated in FIG. 3-5. As illustrated in FIG. 3, a reference electrode material, e.g. a paste 42 containing a suitable electrolyte for the reference electrode redox reaction, such as an Ag/AgCl containing paste, is deposited in the second cavity onto the conductive area 40 exposed by the second cavity 24, which forms the electrolyte source for the redox (half-)reaction at the reference electrode. Non-limiting examples of such a substance include E412 Ag/AgCl ink as provided by the Ercoinc Company, C61003P7 Ag/AgCl paste as provided by Gwent Electrical Materials Ltd. and 5876 screen-printable Ag/AgCl paste as provided by the DuPont Company.

In order to maintain constant levels of the relevant ions at the interface between the reference electrode and its environment e.g. (silver and) chloride ions, an ion reservoir material 44 containing at least the relevant type of ions also present in the reference electrode material 42, e.g. chloride ions in case of an Ag/AgCl containing paste 42, is deposited over the reference electrode material 42. Preferably, the ion reservoir material contains the relevant ion type in high concentrations, e.g. 1 to 4 M, for the material to act as a buffer for the reference electrode. The ion reservoir material 44 may be any suitable material, e.g. a gel such as agar-agar or cellulose, including a dissolved electrolyte, e.g. a chloride salt such as AgCl, KCl or NaCl. The ion reservoir material 44 is used to fill the remainder of the second cavity 24. This is illustrated in FIG. 4.

To avoid the ions in the ion reservoir material 44, e.g. chloride ions, from escaping the second cavity 24, a film or membrane 46 is formed over the second cavity 24 as illustrated in FIG. 5, which may for instance be an ion-selective membrane such as a Nafion® membrane, that is partially or completely impermeable to the relevant ions, e.g., chloride ions, although most standard reference electrodes do not have such a film or membrane. In this embodiment, the film or membrane 46 is permeable to the analyte of interest, i.e. $H^+$ ions, to allow electrical contact between the sample to be measured and the reference electrode as will be readily understood by the skilled person. The film or membrane 46 prohibits or reduces the out-diffusion or leaching of chloride ions from the ion reservoir material, e.g. gel, 44. Thus the potential of the reference electrode maintains constant and the reference electrode functions during its specified lifetime, thus extending the lifetime of the pH sensor. The film or membrane 46 may be kept in place using any suitable fixation technique, e.g. gluing, adhesion or lamination.

Figure 6:
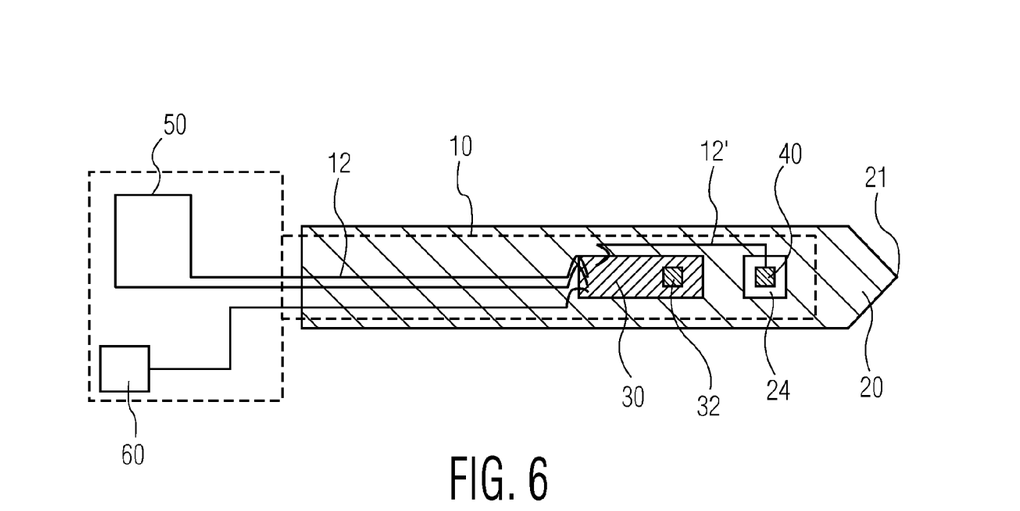
FIG. 6 schematically illustrates a top view of an intermediate device according to another embodiment.

The above described pH sensor may be amended in a number of ways without departing from the scope of the embodiments described herein. One such a design variation is illustrated in FIG. 6, which illustrates a top view of a sensing device 30 that includes a RFID chip connected to an antenna 50, e.g. a loop antenna or any other suitable antenna design, and a power supply 60, e.g. a battery or an induction coil, via respective conductive tracks 12. The antenna 50 and power supply 60 may be placed inside or outside the molding 20.

In this embodiment, the RFID chip may be adapted to process the sensor readings on chip and send pH, conductivity and/or temperature readings to a remote receiver via the antenna 50, such that permanent electrical contact with the pH sensor to obtain sensor readings is unnecessary. In this embodiment, the conductive portion 40 exposed by the second cavity 24, such as a contact pad, of the reference electrode may be connected to the sensing device 30 via a further conductive track 12' to facilitate the on-chip processing of the sensor signals. The wireless connection allows for automated periodic monitoring of the pH of the substance under investigation, which may for instance be advantageous in application domains such as food quality monitoring, where such periodic readings can be used to monitor the deterioration of the food product beyond acceptable levels.

Figure 7:
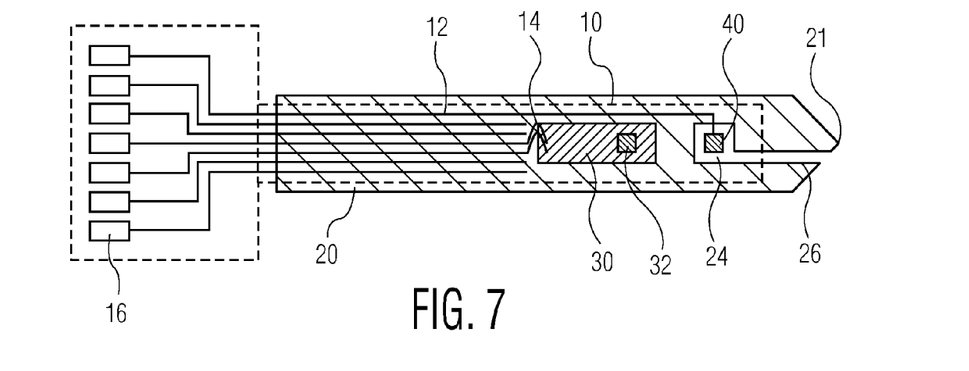
FIG. 7 schematically illustrates a top view of a pH sensor according to yet another embodiment.

Access to the reference electrode of the pH sensor of the embodiments described herein is not limited to a semi-permeable membrane or film 46 sealing or covering the second cavity 24. An alternative embodiment is illustrated in FIG. 7 (top view) and FIG. 8 (cross-section). This embodiment of the pH sensor of the embodiments described herein includes a fluid channel 26 that extends from an edge of the molding 20 to the second cavity 24, such that reference electrode material 42 and the ion reservoir material 44 in the reference electrode are in contact with the analyte of interest through the fluid channel 26. It is noted that the fluid channel 26 is dimensioned such that only a small section of the ion reservoir material 44 is in contact with the analyte of interest, thus preventing or at least reducing the out-diffusion of substantial amounts of chloride ions from the reference electrode.

Figure 8:
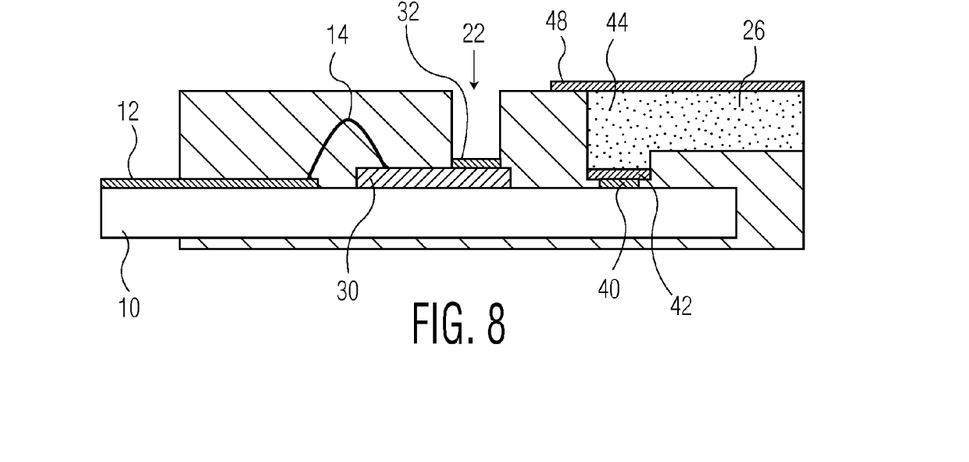
FIG. 8 schematically illustrates a cross section of the pH sensor of FIG. 7.

In case of the presence of the sharp tip 21 at the insertion end of the pH sensor, it is preferred that the fluid channel 26 exits the molding 20 at the edge containing the sharp tip 21, and in such a manner that the fluid channel 26 is off-centered compared to the sharp tip 21, thus avoiding weakening of the sharp tip 21 that could lead to mechanical damage upon insertion of the pH sensor into a substance to be measured, as well as reducing the risk of the fluid channel 26 becoming blocked by the substance penetrating the fluid channel 26 upon insertion of the pH sensor in the substance.

In the embodiment illustrated in FIGS. 7 and 8, it is not necessary that the second cavity 24 is sealed by a (semi-)permeable layer or film 46 (although such a layer or film may still be used). Instead, the second cavity 24 may be sealed by an ion-impermeable film or sheet 48, which may be fixated into place in any suitable manner, e.g. gluing, adhering or laminating. Although the embodiment of FIGS. 7 and 8 is illustrated as a variation to the pH sensor depicted in FIG. 1-5, it is of course equally feasible to apply these variations to the design of the pH sensor illustrated in FIG. 6.

Figure 9:
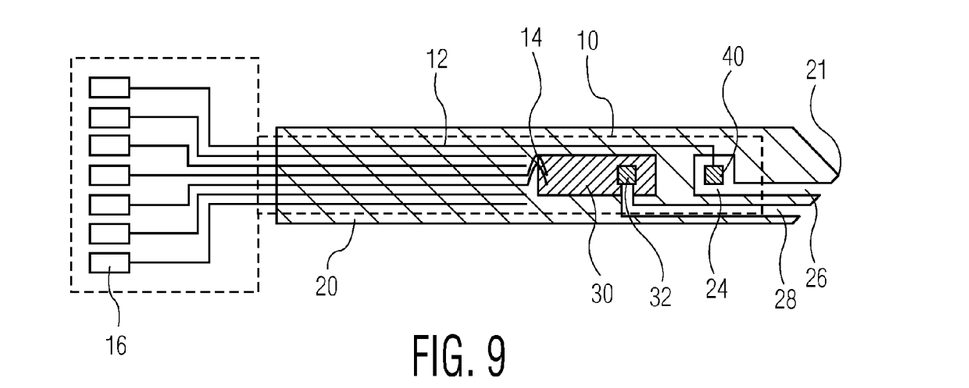
FIG. 9 schematically illustrates a top view of a pH sensor according to a further embodiment.

FIG. 9 illustrates a top view of yet another embodiment of a pH sensor, which is a variation to the design illustrated in FIGS. 7 and 8. Compared to FIGS. 7 and 8, the pH sensor illustrated in FIG. 9 includes a further fluid channel 28 that extends from an edge of the molding 20 to the first cavity 22, such that the pH sensing device and the reference electrode are kept in fluidic contact with each other via the fluid channels 26 and 28. This ensures that a sensing electrode 31 of the exposed surface 32 is kept biased rather than floating due to the fact that a permanent electrical connection between the sensing electrode of the sensing device 30 and the reference electrode is maintained through the sample, i.e. the substance to be measured. The top of the further fluid channel 28 may be sealed with a further film or sheet (not illustrated). Alternatively, the top of the further fluid channel 28 may be kept open as a single open side will only have a limited effect on the capillary force exerted within the further fluid channel 28 as long as this channel has been appropriately dimensioned.

A particular advantageous feature of the embodiments described herein is that the reference electrode of the pH sensor may be formed during the packaging process of the sensor. This has the advantage that the carrier such as a PCB only requires the presence of the conductive portion 40 connected to one of the conductive tracks 12, and that the sensing device 30 does not require complex manufacturing steps and additional area to facilitate the presence of a reference electrode on-chip.

It has been illustrated in FIG. 2-5 how a reference electrode may be formed in a pH sensor package including cavities 22 and 24 respectively exposing a sensing electrode 31 of a sensing device 30 such as an IC die and a conductive area 40 forming the electrode surface of a reference electrode.

Figure 10A:
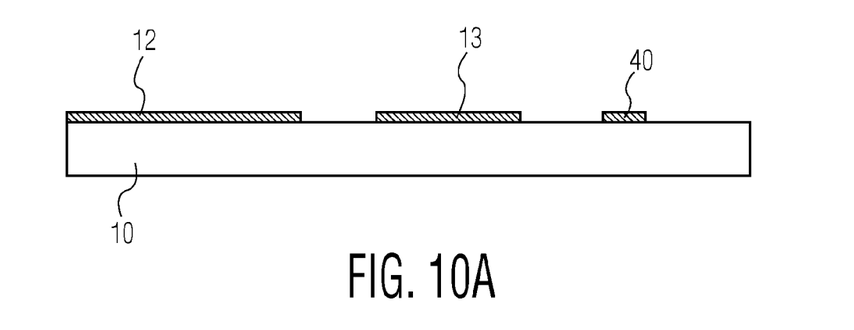
FIGS. 10A-10C schematically illustrate various steps of a method of manufacturing an intermediate device such as illustrated in FIG. 2.
Figure 10B:
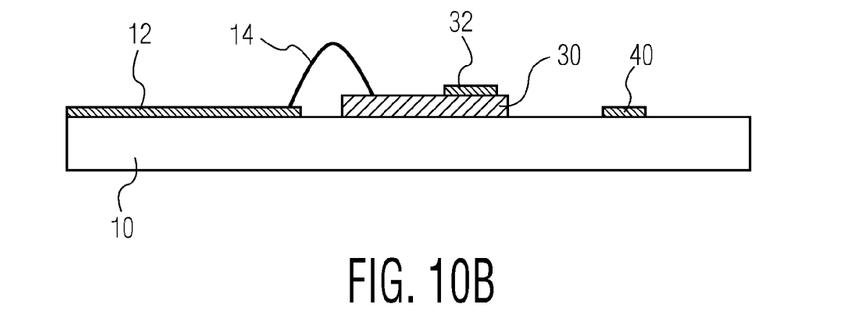
Figure 10C:
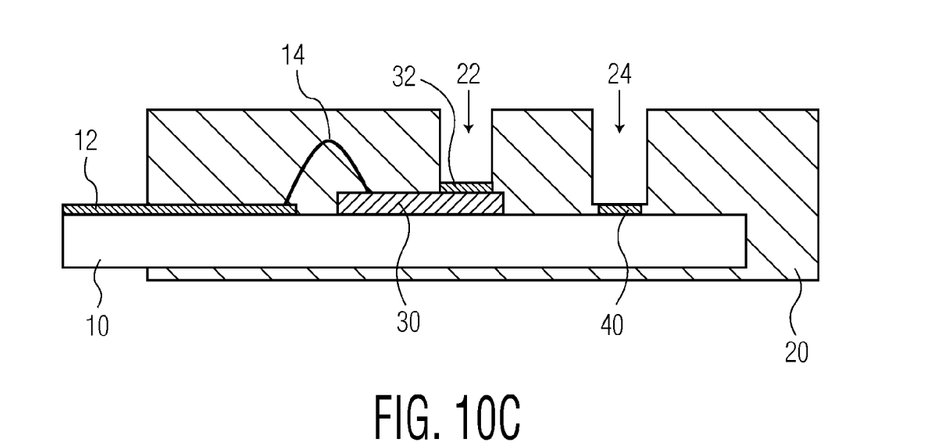

FIGS. 10A-10C schematically illustrate various steps of a method of manufacturing an intermediate device such as illustrated in FIG. 2. As illustrated in FIG. 10A, during chip processing, a carrier 10 is provided such as a PCB, which includes the exposed conductive area 40 in addition to conductive tracks 12 and a further conductive area 13 for receiving a die such as a mounting or landing pad. Such carriers are known in the art and any suitable embodiment of such a carrier may be used. During this processing, the sensing device 30, sensing electrode 31 and electrodes 34 are formed, and deposition of the $TaO_5$ layer is performed.

As illustrated in FIG. 10B, the sensing device 30 is fixated on the exposed conductive area 13, e.g. mounting pad, e.g. adhered, glued or otherwise fixated thereon. The sensing device 30 need not be fixated to the exposed conductive area. The sensing device could also be fixated to an insulative area, or to the carrier. Contacts (not illustrated) of the sensing device 30 are connected to the relevant conductive tracks 12 in any suitable manner, e.g. using bond wires 14. The sensing device 30 typically includes the sensing electrode 31 of the exposed surface 32 that is sensitive to $H^+$ concentrations, e.g. an extended gate of an ISFET.

By additional patterning, electrodes 34 may be formed in addition to the sensing electrode 31. Using AC measurements, the conductivity of an analyte of interest may be determined. A suitable material to be formed atop the exposed surface 32 of the gate electrode 31 and the electrodes 34 is $Ta_2O_5$, although other pH-sensitive materials may be used. Use of $Ta_2O_5$ makes otherwise non-inert electrode materials inert, which allows them to avoid corrosion/attack by aggressive solutions.

As illustrated in FIG. 10C, the carrier 10 with mounted sensing device 30 is encapsulated in encapsulation 20. In a preferred embodiment, the cavities 22 and 24 that expose the sensing electrode 31 of the exposed surface 32, the electrodes 34 and the reference electrode surface 40 respectively are formed simultaneously with the encapsulation 20. This simultaneous step may further include the formation of the fluidic channels 26 and 28 if present. This simultaneous formation may for instance be achieved using a film-assisted molding process such as the so-called Boschman process or other suitable molding processes, e.g. overmolding. Preferably, the mold includes exclusion areas defining the cavities 22 and 24.

In a film-assisted molding process, one or two plastic films are used to protect the mold. This film is sucked down into the inner surfaces of the mold, before the carrier 10 is loaded into the mold. This is followed by a transfer molding process, which is well-known.

The molding material is first liquefied by heat and pressure, and then forced into closed mold cavities and held there under additional heat and pressure until all material is solidified (i.e. cured). After opening the mold, the encapsulated products are unloaded. Film-Assisted Molding offers a number of advantages over conventional transfer molding. These include the easy release of the encapsulated products from the mold, and the fact that surfaces such as the conductive area 40, pH sensitive surface of the exposed surface 32 and contact pads 16 can be kept clear of the molding compound.

Although preferable, it is not essential to the embodiments described herein that the cavities 22 and 24 are formed during the encapsulation process. Alternatively, the cavities 22 and 24 may be formed after the encapsulation 20 is formed, e.g. by means of laser cutting.

Other alternative manufacturing methods may be contemplated. For instance, the carrier 10 may be provided in a pre-molded package 20 in which the sensing device 30 is subsequently placed, and which may be sealed with e.g. an epoxy resin after the formation of the contacts, e.g. bond wires 14, between the sensing device 30 and the conductive tracks 12.

In an additional embodiment, a conductivity sensor is combined with the pH sensor as another way to measure the water quality of a sample being tested. Conductivity measurements are analyzed separately from the measurements of the pH sensing device. In a standard configuration, the electrodes 34 are directly located on the sensing device 30 and connect to underlying electronics with interconnect vias and metal layers.

Figure 11:
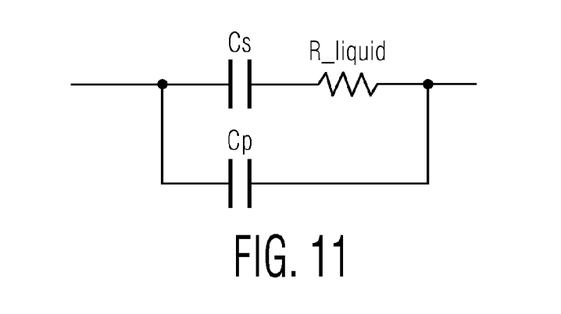
FIG. 11 schematically illustrates an equivalent circuit used to measure the conductivity of a given analyte being tested according to a further embodiment.

FIG. 11 schematically illustrates an equivalent circuit used to measure the conductivity of a given analyte being tested according to a further embodiment. Conductivity measurements may be analyzed using underlying electronics in the chip 30.

To determine conductivity of an analyte of interest, a total impedance of an analyte between any two electrodes 34 is determined using impedance analyzer circuitry, extracting the resistive part of the impedance, which represents the resistance of the analyte. The inverse of the resistance can then be calculated to determine conductance, and therefore the conductivity thereof, as is known in the art. Various conductive lines 34 with different spacings may be utilized to determine different conductances of a given analyte, and various measurements may be taken to achieve the best signal to noise ratio for measurement electronics.

In prior art sensors, noble metals are used to measure qualities of an analyte, as noble metals are typically non-corrosive. However, in CMOS processes, noble metals are typically not used. In the implementation of conductivity sensors, by making use of the same process that is used to form the pH sensors, CMOS compatible metals are used. While these metals may be somewhat corrodible, embodiments described herein provide extra protection for these metals by providing an additional CMOS compatible material that is not necessarily conductive. This extra protection is provided by the $Ta_2O_5$ insulation layer that provides inertness to all the electrode materials used.

Figure 12:
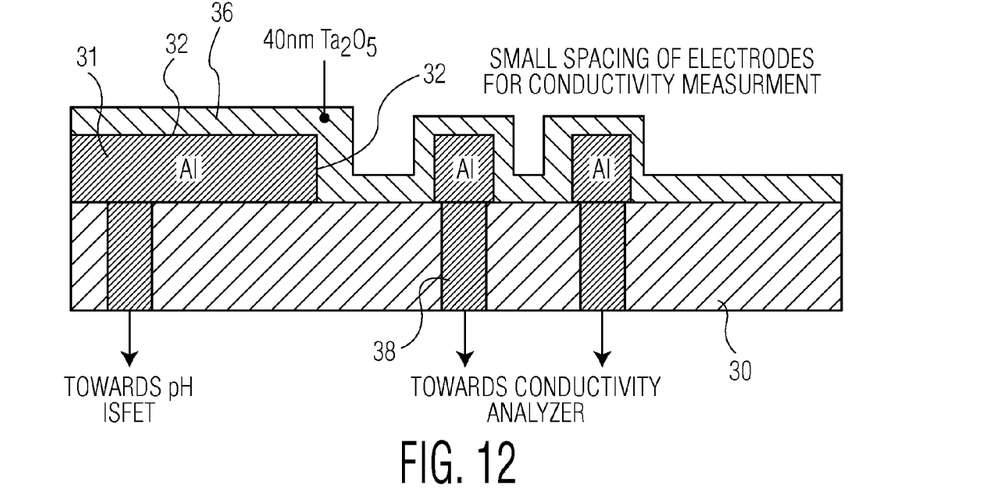
FIGS. 12 and 13 schematically illustrate configurations of the sensing electrode according to a further embodiment.
Figure 13:
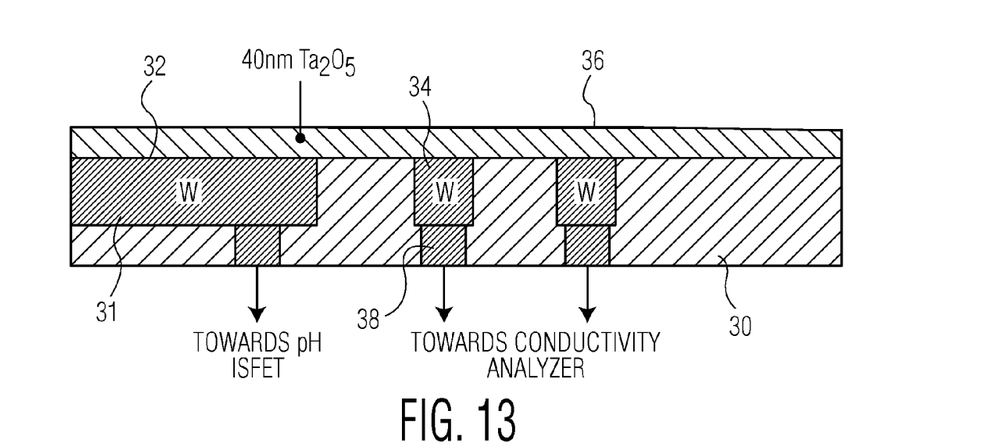

FIGS. 12 and 13 schematically illustrate configurations of the sensing device according to a further embodiment. The sensing device 30 may include the exposed surface 32 of the sensing electrode 31 and a plurality of electrodes 34. The sensing electrode 31, the exposed surface 32 and electrodes 34 may be formed atop the sensing device 30 or may be recessed within the sensing device 30, forming a planar top surface thereof. The sensing electrode 31, and electrodes 34 may be formed of Pt, Al, Al/Cu, W, or other materials known in the art. Interconnection lines 38 are formed between the sensing electrode 31 and the pH ISFET, and between the electrodes 34 and a conductivity analyzer respectively.

Because of the specific build-up of the conductivity sensor, a limited frequency window can be defined, where the resistance of the liquid or analyte of interest contributes to the total measured impedance. To improve accuracy or to isolate the liquid resistance, impedance fitting may be performed to extract the resistance of the liquid. The conductivity of the analyte may be determined by determining an overall impedance between two electrodes 34 and compensating for a capacitance of the substrate and a capacitance of the protection layer As illustrated in FIG. 12, parallel interconnect lines 34 of Al or equivalent metal may have an exemplary length of 10 cm and a separation of 1 micron. Using the equivalent circuit illustrated in FIG. 11, whereby $R_{liquid}$ represents the resistance of the liquid, which is inversely proportional to the conductivity of the liquid, Cs is the series capacitance originating from the $Ta_2O_5$ protective layer 36 and Cp is the parallel capacitance from the passivation stack/substrate. The protective layer capacitance and the parallel capacitance should be tuned such that $R_{liquid}$ is maximally visible in the frequency window between 1 kHz to 1 MHz.

Calibration of the sensor should be done by measuring the impedance (or if extracted from impedance spectrum fitting: by measuring the resistance) of the two-electrode sensor when exposed to a conductivity calibration electrolyte. From this one measurement point, the cell parameter can be derived. The cell parameter is the proportionality factor between resistance/conductance and specific resistivity/conductivity.

A temperature sensor may also be formed in the pH sensor device of the embodiments described herein. Along with the readout of the pH sensor and conductivity sensor may be temperature sensor readout. Voltage output from the pH sensor and the resistance values of the conductivity sensor are very temperature dependent. Underneath the pH sensing layer and the conductivity sensing layer are read out electronics, and part of the readout electronics are able to determine a temperature of the analyte based a separate temperature sensor integrated into the substrate, such as a PTAT device.

The user interface of the pH sensor connected via contact pads 16 may be configured to display readouts of pH levels, conductivity, and temperature of a given analyte.

It should be apparent from the foregoing description that various exemplary embodiments of the invention may be implemented in hardware. Furthermore, various exemplary embodiments may be implemented as instructions stored on a non-transitory machine-readable storage medium, such as a volatile or non-volatile memory, which may be read and executed by at least one processor to perform the operations described in detail herein. A machine-readable storage medium may include any mechanism for storing information in a form readable by a machine, such as a personal or laptop computer, a server, or other computing device. Thus, a non-transitory machine-readable storage medium excludes transitory signals but may include both volatile and non-volatile memories, including but not limited to read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware including several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A pH and conductivity sensor comprising:
   a carrier comprising a plurality of conductive tracks and an exposed conductive area defining a reference electrode connected to a first track of said plurality of conductive tracks;
   a sensing device mounted on the carrier and connected to at least a second track of said plurality of conductive tracks, the sensing device comprising:
      an exposed surface that is sensitive to $H^+$ concentrations; and
      a plurality of electrodes adjacent to the exposed surface;
   an encapsulation covering the carrier, said encapsulation comprising:
      a first cavity exposing a surface of the sensing device, and
      a second cavity exposing the exposed conductive area.

2. The ph and conductivity sensor of claim 1, wherein the second cavity comprises a reference electrode material and an ion reservoir material that share at least one ion type with said reference electrode material, the reference electrode material being positioned between the exposed conductive area and the ion reservoir material.

3. The pH and conductivity sensor of claim 2, further comprising:
   a layer impermeable to the at least one ion type in the ion reservoir material over the second cavity.

4. The pH and conductivity sensor of claim 3, further comprising:
   an ion-selective membrane impermeable to the at least one ion type in the ion reservoir material over the second cavity.

5. The pH and conductivity sensor of claim 2, wherein the reference electrode material comprises Ag and AgCl and the ion reservoir material comprises chloride ions.

6. The pH and conductivity sensor of claim 1, further comprising:

a first contact pad connected to the sensing device via the second track; and a second contact pad connected to the exposed conductive area via the first track.

7. The pH and conductivity sensor of claim 1, wherein the plurality of electrodes are arranged in parallel.

8. The pH and conductivity sensor of claim 1, wherein the plurality of electrodes are interdigitated.

9. The pH and conductivity sensor of claim 1, wherein said encapsulation further comprises:

a first fluid channel laterally extending from an edge of said encapsulation to the second cavity.

10. The pH and conductivity sensor of claim 9, wherein said encapsulation further comprises:

a second fluid channel laterally extending from said edge to the first cavity.

11. The pH and conductivity sensor of claim 10, wherein the first fluid channel and the second fluid channel maintain a permanent electrical connection between the sensing device and the reference electrode.

12. The pH and conductivity sensor of claim 1, wherein the sensing device comprises an ion sensitive field effect transistor (ISFET) having its gate exposed in the first cavity.

13. The pH and conductivity sensor of claim 12, wherein the gate of the ISFET comprises $Ta_2O_5$.

14. The pH and conductivity sensor of claim 1, further comprising:

a protective layer of $Ta_2O_5$ formed on the plurality of electrodes.

15. A method of manufacturing the pH and conductivity sensor of claim 1, comprising:

providing a carrier having on its surface a plurality of conductive tracks, a first exposed conductive area connected to one of said conductive tracks and a second exposed conductive area;

fixating an integrated circuit die to the carrier, said integrated circuit die comprising an exposed pH-sensitive surface and a plurality of electrodes adjacent to the pH-sensitive surface;

encapsulating the resultant structure in a protective resin;

forming first and second cavities in said protective resin, the first cavity exposing the pH-sensitive surface and the plurality of electrodes and the second cavity exposing the first exposed conductive area;

depositing a reference electrode material over the first exposed conductive area; and depositing an ion reservoir material sharing at least one ion type with said reference electrode material over said reference electrode material.

16. The method of claim 15, wherein said encapsulating step and said forming step are performed simultaneously.

17. A method for measuring a pH and conductivity of an analyte on a substrate using the pH and conductivity sensor of claim 1, the method comprising:

exposing a conductive area defining a reference electrode to an analyte of interest;

exposing a sensing device comprising a pH-sensitive surface, a plurality of electrodes, and a protection layer to the analyte of interest;

determining the pH of the analyte of interest based on measurements taken by the reference electrode and the sensing device; and determining the conductivity of the analyte by determining an overall impedance between the electrodes.

18. The method of claim 17, wherein the protection layer is formed on the pH-sensitive surface and the plurality of electrodes.

19. The method of claim 17, wherein a resistance of the analyte is determined by compensating for a capacitance of the substrate and a capacitance of the protection layer.

20. The method of claim 17, further comprising:

determining a temperature of the analyte based on measurements taken by the reference electrode and the sensing device.

* * * * *